(12) United States Patent
Selaru et al.

(10) Patent No.: US 8,679,759 B2
(45) Date of Patent: Mar. 25, 2014

(54) ESOPHAGEAL CANCER MARKERS

(75) Inventors: Florin M. Selaru, Baltimore, MD (US); Stephen J. Meltzer, Lutherville, MD (US)

(73) Assignees: The Johns Hopkins University, Baltimore, MD (US); University of Maryland, Baltimore, Baltimore, MD (US)

( * ) Notice: Subject to any disclaimer, the term of this patent is extended or adjusted under 35 U.S.C. 154(b) by 570 days.

(21) Appl. No.: 12/671,406

(22) PCT Filed: Jul. 31, 2008

(86) PCT No.: PCT/US2008/071768
§ 371 (c)(1), (2), (4) Date: Jul. 26, 2010

(87) PCT Pub. No.: WO2009/018446
PCT Pub. Date: Feb. 5, 2009

(65) Prior Publication Data
US 2010/0285466 A1    Nov. 11, 2010

Related U.S. Application Data

(60) Provisional application No. 60/953,298, filed on Aug. 1, 2007.

(51) Int. Cl.
*C12Q 1/68* (2006.01)
*G01N 33/53* (2006.01)

(52) U.S. Cl.
USPC ............................ 435/6.14; 435/6.11; 435/7.1

(58) Field of Classification Search
None
See application file for complete search history.

(56) References Cited

U.S. PATENT DOCUMENTS

| | | | | |
|---|---|---|---|---|
| 2001/0029020 | A1* | 10/2001 | Waldman et al. | 435/6 |
| 2002/0110821 | A1* | 8/2002 | Ebner | 435/6 |
| 2006/0168670 | A1* | 7/2006 | Lee et al. | 800/11 |
| 2006/0199210 | A1 | 9/2006 | Weichselbaum et al. | |
| 2006/0211019 | A1 | 9/2006 | Halling et al. | |
| 2007/0105133 | A1 | 5/2007 | Clarke et al. | |
| 2008/0081333 | A1* | 4/2008 | Mori et al. | 435/6 |

OTHER PUBLICATIONS

Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
PCT/US08/71768, International Search Report, Oct. 2008.

* cited by examiner

*Primary Examiner* — James Martinell
(74) *Attorney, Agent, or Firm* — Banner & Witcoff, Ltd.

(57) ABSTRACT

The present invention is directed to methods for diagnosing cancer in a subject. Morphologically normal epithelial cells of the esophagus are assayed for marker expression. Characteristic expression of the markers indicates the presence of cancer or the predisposition to cancer. A panel of eleven markers are particularly good at identifying cancer and the predisposition to cancer.

17 Claims, 3 Drawing Sheets

ESOPHAGEAL CANCER MARKERS

This application claims the benefit of U.S. provisional application 60/953,298 filed Aug. 1, 2007. The contents of the prior application are expressly incorporated herein.

The invention was made with support of a grant from the National Institutes of Health, Grant No: CA001808. The U.S. Government retains certain rights in this invention.

BACKGROUND OF THE INVENTION

One of the greatest challenges in the management of Barrett's esophagus (BA), the precursor lesion of esophageal adenocarcinoma (EAC), is to expeditiously identify patients who have early EAC and to predict those who will develop EAC. The rate of progression to cancer (0.4-0.5% per year in some studies, 0.5 to 1% per year in other studies) is very low, making this challenge particularly difficult (Reynolds et al., *Gastroenterol Clin North Am* 28(4):917-45 (1999); Cameron, *Gastroenterol Clin North Am* 26(3):487-94 (1997)). Moreover, in the surveillance of BA, a meticulous endoscopic search is often performed to identify grossly normal-appearing dysplastic or cancerous lesions. However, the value of this type of systematic surveillance has been questioned, due to its low sensitivity and specificity (Conio et al., *Am J Gastroenterol* 98(9):1931-9 (2003)). Thus, from a purely practical standpoint, it would be advantageous to be able to identify patients with malignant esophageal lesions simply by biopsying their normal squamous esophagus.

The presence and degree of dysplasia constitute the most widely accepted measure of neoplastic risk in Barrett's esophagus. However, significant problems have emerged demonstrating the need for improved progression risk biomarkers. These problems include poor interobserver reproducibility of dysplasia interpretation and inconsistent rates of progression as well as regression of dysplasia, both of which have made it difficult to develop national surveillance guidelines (Conio et al., *Am J Gastroenterol* 98(9):1931-9 (2003); Rana et al., *Dis Esophagus* 13(1):28-31 (2000); Reid et al., *Am J* Gastroenterol 95(7):1669-76 (2000)). Flow cytometry has shown promise in detecting a subset of patients who do not have high-grade dysplasia (HGD) but do have an increased risk of progression (Reid et al., *Am J Gastroenterol* 95(7):1669-76 (2000)).

The human genome project has yielded high-throughput methodologies for the computer analysis of data, which provide volume and quality control required to select clinically useful biomarkers (Taramelli et al., *Eur J Cancer* 40(17): 2537-43 (2004); Varmus et al., *Science* 310(5754):1615 (2005); Yoshida, *Jpn J Clin Oncol* 29(10):457-9 (1999)). 17p (p53)-loss of heterozygosity (LOH) has also shown potential as a molecular biomarker (Reid et al., *Gastrointest Endosc Clin N Am* 13(2):369-97 (2003)). In addition, methylation of p16 and HPP1 have been shown to predict progression to HGD and EAC (Hardie et al., *Cancer Lett* 217(2):221-30 (2005); Geddert et al., *Int J Cancer* 110(2):208-11 (2004); Schulmann et al., *Oncogene* 24(25):4138-48 (2005)). Molecular alterations have been found in Barrett's metaplasia which reveal a field effect in premalignant metaplastic mucosa, but not in normal epithelium. For example, aneuploidy and loss of heterozygosity have been observed in metaplastic mucosa from Barrett's patients with dysplasia or adenocarcinoma (Blount et al., *Proc Natl Acad Sci USA* 90(8):3221-5 (1993); Boynton et al., *Cancer Res* 51(20): 5766-9 (1991); Raskind et al., *Cancer Res* 52(10):2946-50 (1992); Reid et al., *Gastroenterology* 93(1):1-11 (1987)). Similarly, p53 tumor suppressor gene point mutations have been reported in Barrett's metaplasia (Casson et al., *Am J Surg* 167(1):52-7 (1994); Huang et al., *Cancer Res* 53(8): 1889-94 (1993); Meltzer et al., *Proc Natl Acad Sci USA* 88(11):4976-80 (1991)), and altered promoter DNA methylation has also been described for some tumor suppressor genes in Barrett's esophagus (Eads et al., *Cancer Res* 60(18): 5021-6 (2000); Kawakami et al., *J Natl Cancer Inst* 92(22): 1805-11 (2000); Klump et al., *Gastroenterology* 115:1381-6 (1998); Wong et al., *Cancer Res* 57(13):2619-22 (1997)).

In contrast, most published studies to date report no DNA alterations (e.g., point mutations, methylation, or loss of heterozygosity) in normal squamous esophageal epithelium from patients with esophageal cancer. Corn et al. (*Clinical Cancer Research* 7(9):2765-9 (2001)) reported E-cadherin methylation in Barrett's esophagus specimens and esophageal adenocarcinoma, but not in normal esophageal epithelium. Another study showed that the expression of a panel of 23 genes capable of differentiating between Barrett's esophagus and esophageal adenocarcinoma was unable to distinguish between the normal epithelia of Barrett's metaplasia and adenocarcinoma patients (Brabender et al., *Oncogene* 23(27):4780-8 (2004)). One notable exception was the study by Eads et al., which found methylation of the CALCA, MGMT, and TIMP3 genes in the normal esophagus of a subset of patients with Barrett's-associated esophageal dysplasia and adenocarcinoma (Eads et al., *Cancer Res* 61(8): 3410-8 (2001).

cDNA microarrays promise more accurate prediction than do classical clinical diagnostic tools (such as histologic categorization). However, the main challenge posed by microarrays is to construct meaningful classifiers based on gene expression profiles, using appropriate bioinformatics tools. A number of bioinformatics tools have been proposed, including artificial neural networks (Selaru et al., *Gastroenterology* 122(3):606-13 (2002)), hierarchical clustering (Selaru et al., *Oncogene* 21(3):475-8 (2002); Zou et al., *Oncogene* 21(31): 4855-62 (2002)) and principal components analysis (Mori et al., *Cancer Res* 63(15):4577-82 (2003); Selaru et al., *Cancer Res* 64:1584-88 (2004)). Shrunken nearest centroid predictors (SNCPs) were adapted from classical nearest centroids predictors to gene microarray analysis (Tibshirani et al., *Proc Natl Acad Sci USA* 99(10):6567-72 (2002)). From among large numbers of genes, it is difficult to distinguish expression variations due to chance. However, these variations tend to be of small amplitude. Thus, if small variations are ignored and only consistently relatively high changes in expression are accepted, biologic changes prevail over variations due to chance. Among the mathematical means used to ignore small variations, one method, SNCPs, is particularly valuable. Prediction Analysis of Microarrays (PAM) is a software package developed at Stanford University that utilizes SNCPs and performs internal validation simultaneously. Samples are divided up at random into K roughly equal-sized parts. For each part in turn, the classifier is built on the remaining K-1 parts, then tested on the last 1 part. This procedure is performed over a range of threshold values, and the cross-validated misclassification error rate is reported for each threshold value. Typically, the user chooses the threshold value giving the minimum cross-validated misclassification error rate. This method has been utilized successfully by investigators studying leukemia and breast cancer to find subsets of genes that accurately predicted classifications of these diseases (Tibshirani et al., *Proc Natl Acad Sci USA* 99(10):6567-72 (2002); Korkola et al., *Cancer Res* 63(21):7167-75 (2003); Sorlie et al., *Proc Natl Acad Sci USA* 100(14):8418-23 (2003)).

SUMMARY OF THE INVENTION

Diagnosing Cancer—Different Subjects

The present invention is directed to a method for diagnosing cancer in a subject comprising (a) determining a gene expression pattern of a biological sample from a subject, and (b) comparing the gene expression pattern of (a) with a gene expression pattern of a biological sample from a subject that does not have cancer using shrunken nearest centroid predictors, wherein when differential gene expression is detected, the subject is diagnosed as having cancer.

The present invention is also directed to a method for diagnosing esophageal adenocarcinoma in a subject comprising (a) determining a gene expression pattern of esophageal epithelium from a subject, and (b) comparing the gene expression pattern of (a) with a gene expression pattern of esophageal epithelium from a subject that does not have cancer, wherein when differential gene expression is detected, the subject is diagnosed as having esophageal adenocarcinoma.

The present invention is further directed to a method for diagnosing esophageal adenocarcinoma in a subject comprising (a) determining a gene expression pattern of esophageal epithelium from a subject, and (b) comparing the gene expression pattern of (a) with a gene expression pattern of esophageal epithelium from a subject that does not have cancer using shrunken nearest centroid predictors, wherein when differential gene expression is detected, the subject is diagnosed as having esophageal adenocarcinoma.

Diagnosing Cancer—Same Subject

The present invention is directed to a method for diagnosing cancer in a subject comprising (a) determining a gene expression pattern of a first biological sample from a subject, and (b) comparing the gene expression pattern of (a) with a gene expression pattern of a second biological sample from the subject using shrunken nearest centroid predictors, wherein when differential gene expression is detected, the subject is diagnosed as having cancer.

The present invention is directed to a method for diagnosing esophageal adenocarcinoma in a subject comprising (a) determining a gene expression pattern of a first sample of esophageal epithelium from a subject, and (b) comparing the gene expression pattern of (a) with a gene expression pattern of a second sample of esophageal epithelium from the subject, wherein when differential gene expression is detected, the subject is diagnosed as having esophageal adenocarcinoma.

The present invention is directed to a method for diagnosing esophageal adenocarcinoma in a subject comprising (a) determining a gene expression pattern of a first sample of esophageal epithelium from a subject, and (b) comparing the gene expression pattern of (a) with a gene expression pattern of a second sample of esophageal epithelium from the subject using shrunken nearest centroid predictors, wherein when differential gene expression is detected, the subject is diagnosed as having esophageal adenocarcinoma.

The present invention is directed to a method for diagnosing cancer in a subject comprising (a) determining a gene expression pattern of a first biological sample from a subject, and (b) comparing the gene expression pattern of (a) with a gene expression pattern of a second biological sample from the subject using shrunken nearest centroid predictors, wherein when differential gene expression is detected, the subject is diagnosed as having cancer, and wherein the locations from which the first and second biological samples are obtained are separated by a distance of at least 3 cm in said subject.

The present invention is directed to a method for diagnosing esophageal adenocarcinoma in a subject comprising (a) determining a gene expression pattern of a first sample of esophageal epithelium from a subject, and (b) comparing the gene expression pattern of (a) with a gene expression pattern of a second sample of esophageal epithelium from the subject, wherein when differential gene expression is detected, the subject is diagnosed as having esophageal adenocarcinoma, and wherein the locations from which the first and second biological samples are obtained from the esophageal epithelium are separated by a distance of at least 3 cm in said subject.

The present invention is directed to a method for diagnosing esophageal adenocarcinoma in a subject comprising (a) determining a gene expression pattern of a first sample of esophageal epithelium from a subject, and (b) comparing the gene expression pattern of (a) with a gene expression pattern of a second sample of esophageal epithelium from the subject using shrunken nearest centroid predictors, wherein when differential gene expression is detected, the subject is diagnosed as having esophageal adenocarcinoma, and wherein the locations from which the first and second biological samples are obtained from the esophageal epithelium are separated by a distance of at least 3 cm in said subject.

The present invention is directed to a method for diagnosing cancer in a subject comprising (a) determining a gene expression pattern of a first biological sample from a subject, and (b) comparing the gene expression pattern of (a) with a gene expression pattern of a second biological sample from the subject using shrunken nearest centroid predictors, wherein when differential gene expression is detected, the subject is diagnosed as having cancer, and wherein the locations from which the first and second biological samples are obtained have a grossly different appearance.

The present invention is directed to a method for diagnosing esophageal adenocarcinoma in a subject comprising (a) determining a gene expression pattern of a first sample of esophageal epithelium from a subject, and (b) comparing the gene expression pattern of (a) with a gene expression pattern of a second sample of esophageal epithelium from the subject, wherein when differential gene expression is detected, the subject is diagnosed as having esophageal adenocarcinoma, and wherein the locations from which the first and second biological samples are obtained from the esophageal epithelium have a grossly different appearance.

The present invention is directed to a method for diagnosing esophageal adenocarcinoma in a subject comprising (a) determining a gene expression pattern of a first sample of esophageal epithelium from a subject, and (b) comparing the gene expression pattern of (a) with a gene expression pattern of a second sample of esophageal epithelium from the subject using shrunken nearest centroid predictors, wherein when differential gene expression is detected, the subject is diagnosed as having esophageal adenocarcinoma, and wherein the locations from which the first and second biological samples are obtained from the esophageal epithelium have a grossly different appearance.

Detecting Differential Gene Expression

The present invention is also directed to a method for detecting differential gene expression in a subject comprising (a) determining a gene expression pattern of a biological sample from a subject, and (b) comparing the gene expression pattern of (a) with a pre-determined gene expression pattern using shrunken nearest centroid predictors, wherein when the gene expression pattern of (a) is different from the pre-determined gene expression pattern, differential gene expression is detected.

The present invention is also directed to a method for detecting differential gene expression in a subject comprising (a) determining a gene expression pattern of esophageal epithelium from a subject, and (b) comparing the gene expression pattern of (a) with a pre-determined gene expression pattern of esophageal epithelium, wherein when the gene expression pattern of (a) is different from the pre-determined gene expression pattern, differential gene expression is detected.

The present invention is also directed to a method for detecting differential gene expression in a subject comprising (a) determining a gene expression pattern of esophageal epithelium from a subject, and (b) comparing the gene expression pattern of (a) with a pre-determined gene expression pattern of esophageal epithelium using shrunken nearest centroid predictors, wherein when the gene expression pattern of (a) is different from the pre-determined gene expression pattern, differential gene expression is detected.

Diagnosing Cancer Using Markers

The present invention is directed to a method for diagnosing cancer in a subject comprising (a) determining an expression pattern of one or more genes in a biological sample from a subject, and (b) comparing the expression pattern of (a) with an expression pattern of the one or more genes in a biological sample from a subject that does not have cancer using shrunken nearest centroid predictors, wherein when differential gene expression is detected, the subject is diagnosed as having cancer.

The present invention is directed to a method for diagnosing esophageal adenocarcinoma in a subject comprising (a) determining an expression pattern of one or more genes in esophageal epithelium from a subject, and (b) comparing the expression pattern of (a) with an expression pattern of the one or more genes in esophageal epithelium from a subject that does not have esophageal adenocarcinoma, wherein when differential gene expression is detected, the subject is diagnosed as having esophageal adenocarcinoma.

The present invention is directed to a method for diagnosing esophageal adenocarcinoma in a subject comprising (a) determining an expression pattern of one or more genes in esophageal epithelium from a subject, and (b) comparing the expression pattern of (a) with an expression pattern of the one or more genes in esophageal epithelium from a subject that does not have esophageal adenocarcinoma using shrunken nearest centroid predictors, wherein when differential gene expression is detected, the subject is diagnosed as having esophageal adenocarcinoma.

The present invention is also directed to a method for diagnosing esophageal adenocarcinoma in a subject comprising (a) determining an expression pattern of one or more genes in esophageal epithelium from a subject, and (b) comparing the expression pattern of (a) with an expression pattern of the one or more genes in esophageal epithelium from a subject that does not have esophageal adenocarcinoma, wherein when differential gene expression is detected, the subject is diagnosed as having esophageal adenocarcinoma, and wherein the one or more genes are genes selected from Table 1.

The present invention is also directed to a method for diagnosing esophageal adenocarcinoma in a subject comprising (a) determining an expression pattern of one or more genes in esophageal epithelium from a subject, and (b) comparing the expression pattern of (a) with an expression pattern of the one or more genes in esophageal epithelium from a subject that does not have esophageal adenocarcinoma using shrunken nearest centroid predictors, wherein when differential gene expression is detected, the subject is diagnosed as having esophageal adenocarcinoma, and wherein the one or more genes are genes selected from Table 1.

TABLE 1

| Name | Gene ID |
|---|---|
| gravin, complete cds. | AB003476 |
| protease, serine, 22 (P11) | XM_006625 |
| H1 histone family, member 2 (H1F2) | NM_005319 |
| fucosyltransferase 1 (galactoside 2-alpha-L-fucosyltransferase, Bombay phenotype included) (FUT1) | NM_000148 |
| H2A histone family, member L (H2AFL) | XM_004416 |
| serine (or cysteine) proteinase inhibitor, clade B (ovalbumin), member 2 (SERPINB2) | NM_002575 |
| H2B histone family, member C (H2BFC) | NM_003519 |
| membrane associated guanylate kinase 2 (MAGI-2) | AF038563 |
| (RG) heterogeneous nuclear ribonucleoprotein H1 (H) | R11019 |
| keratin 8 (KRT8) | NM_002273 |
| RAD51 (*S. cerevisiae*) homolog (*E coli* RecA homolog) (RAD51) | XM_031515 |
| plasminogen activator, urokinase (PLAU) | NM_002658 |
| H3 histone family, member B (H3FB) | NM_003530 |
| aldehyde dehydrogenase 1 family, member A3 (ALDH1A3) | XM_017971 |
| (RG) ankyrin 1, erythrocytic | AA464755 |
| wild-type p53 activated fragment-1 (WAF1) | U03106 |
| like mouse brain protein E46 (E46L) | NM_013236 |
| progestin induced protein (DD5) | NM_015902 |
| H2A histone family, member O (H2AFO) | NM_003516 |
| transglutaminase 3 (TGM3) | XM_009572 |
| major histocompatibility complex, class II, DR alpha (HLA-DRA) | NM_019111 |
| mitotic checkpoint protein kinase BUB1B (BUB1B) | AF107297 |
| glutathione peroxidase 2 (gastrointestinal) (GPX2) | NM_002083 |

The present invention is also directed to a method for diagnosing esophageal adenocarcinoma in a subject comprising (a) determining an expression pattern of one or more genes in esophageal epithelium from a subject, and (b) comparing the expression pattern of (a) with an expression pattern of the one or more genes in esophageal epithelium from a subject that does not have esophageal adenocarcinoma, wherein when differential gene expression is detected, the subject is diagnosed as having esophageal adenocarcinoma, and wherein the one or more genes are genes selected from Table 2.

The present invention is also directed to a method for diagnosing esophageal adenocarcinoma in a subject comprising (a) determining an expression pattern of one or more genes in esophageal epithelium from a subject, and (b) comparing the expression pattern of (a) with an expression pattern of the one or more genes in esophageal epithelium from a subject that does not have esophageal adenocarcinoma using shrunken nearest centroid predictors, wherein when differential gene expression is detected, the subject is diagnosed as having esophageal adenocarcinoma, and wherein the one or more genes are genes selected from Table 2.

TABLE 2

| Name | Gene ID |
|---|---|
| gravin, complete cds. | AB003476 |
| protease, serine, 22 (P11) | XM_006625 |
| H1 histone family, member 2 (H1F2) | NM_005319 |
| fucosyltransferase 1 (galactoside 2-alpha-L-fucosyltransferase, Bombay phenotype included) (FUT1) | NM_000148 |

TABLE 2-continued

| Name | Gene ID |
|---|---|
| H2A histone family, member L (H2AFL) | XM_004416 |
| serine (or cysteine) proteinase inhibitor, clade B (ovalbumin), member 2 (SERPINB2) | NM_002575 |
| H2B histone family, member C (H2BFC) | NM_003519 |
| membrane associated guanylate kinase 2 (MAGI-2) | AF038563 |
| (RG) heterogeneous nuclear ribonucleoprotein H1 (H) | R11019 |
| keratin 8 (KRT8) | NM_002273 |
| RAD51 (*S. cerevisiae*) homolog (*E coli* RecA homolog) (RAD51) | XM_031515 |
| plasminogen activator, urokinase (PLAU) | NM_002658 |
| H3 histone family, member B (H3FB) | NM_003530 |
| aldehyde dehydrogenase 1 family, member A3 (ALDH1A3) | XM_017971 |
| (RG) ankyrin 1, erythrocytic | AA464755 |
| wild-type p53 activated fragment-1 (WAF1) | U03106 |
| like mouse brain protein E46 (E46L) | NM_013236 |

In one embodiment a method is provided for determining presence or predisposition to esophageal cancer in a human subject. Expression of one or more genes is determined in a sample of morphologically normal esophageal epithelial cells of a human subject. A composite score of expression of the one or more genes is calculated. The composite score is compared to predetermined values for esophageal cancer or predisposition to esophageal cancer which were obtained using appropriate populations of subjects with esophageal cancer or with predisposition to esophageal cancer. The presence or predisposition to esophageal cancer is identified based on the composite score.

In another embodiment a method is provided for determining presence or predisposition to esophageal cancer in a human subject. Expression of one or more genes is determined in a sample of esophageal epithelial cells of a human subject. The one or more genes is selected from the group consisting of gravin; H1 histone family, member 2 (H1F2); H2A histone family, member L (H2AFL); H2B histone family, member C (H2BFC); keratin 8 (KRT8); progestin induced protein (DD5); H2A histone family, member O (H2AFO); transglutaminase 3 (TGF3); major histocopatibility complex, class II, DR alpha (HLA-DRA); mitotic checkpoint protein kinase BUB1B (BUB1B); and glutathione peroxidase 2 (gastrointestinal) (GPX2). A composite score of expression of the one or more genes is calculated. The composite score is compared to predetermined values for esophageal cancer or predisposition to esophageal cancer which were obtained using appropriate populations of subjects with esophageal cancer or with predisposition to esophageal cancer. The presence or predisposition to esophageal cancer is identified based on the composite score.

Still another embodiment provides a method for determining presence or predisposition to esophageal cancer in a human subject. Expression of one or more genes is determined in a sample of morphologically normal esophageal epithelial cells of a human subject. The one or more genes is selected from the group consisting of gravin; H1 histone family, member 2 (H1F2); H2A histone family, member L (H2AFL); H2B histone family, member C (H2BFC); keratin 8 (KRT8); progestin induced protein (DD5); H2A histone family, member O (H2AFO); transglutaminase 3 (TGF3); major histocompatibility complex, class II, DR alpha (HLA-DRA); mitotic checkpoint protein kinase BUB (BUB1B); and glutathione peroxidase 2 (gastrointestinal) (GPX2). A composite score of expression of the one or more genes is calculated. The composite score is compared to predetermined values for esophageal cancer or predisposition to esophageal cancer which were obtained using appropriate populations of subjects with esophageal cancer or with predisposition to esophageal cancer. Presence or predisposition to esophageal cancer is identified based on the composite score.

Unless otherwise stated, the cancer may be any cancer. The cancer may be esophageal adenocarcinoma or squamous cell cancer of the esophagus.

Unless otherwise stated, in each of the embodiments of the present invention the subject may be a mammal. In some embodiments the subject is a human.

Unless otherwise stated, in each of the embodiments of the present invention the gene expression pattern may be determined by any method known in the art. Either protein or mRNA expression can be analyzed. Any biochemical technique for assaying particular proteins or mRNA species can be used. Gene expression patterns may be determined using a polynucleotide microarray.

Unless otherwise stated, the gene expression pattern may be compared and/or analyzed by shrunken nearest centroid predictors (SNCP). Permutation analysis may be used in addition to SNCP analysis.

Unless otherwise stated, in each of the embodiments of the present invention the biological sample may be any biological sample from which polynucleotides may be obtained, such as mucosa. In some embodiments, the biological sample has a morphologically-normal appearance. In some embodiments the biological sample is esophageal epithelium, or squamous esophageal epithelium. In additional embodiments the biological sample is morphologically-normal appearing esophageal epithelium, or morphologically-normal appearing squamous esophageal epithelium.

Unless otherwise stated, in each of the embodiments of the present invention directed to methods for detecting differential gene expression, the method may further comprise predicting an increased risk for developing cancer in the subject. In one embodiment, the increased risk for developing cancer is an increased risk for developing esophageal adenocarcinoma.

Unless otherwise stated, in each of the embodiments of the present invention the one or more genes used in the determination of an expression pattern may be any of those identified by shrunken nearest centroid predictors. In some embodiments the one or more genes used in the determination of an expression pattern are selected from those genes set forth in Table 1, or selected from those genes set forth in Table 2.

Figure 1:
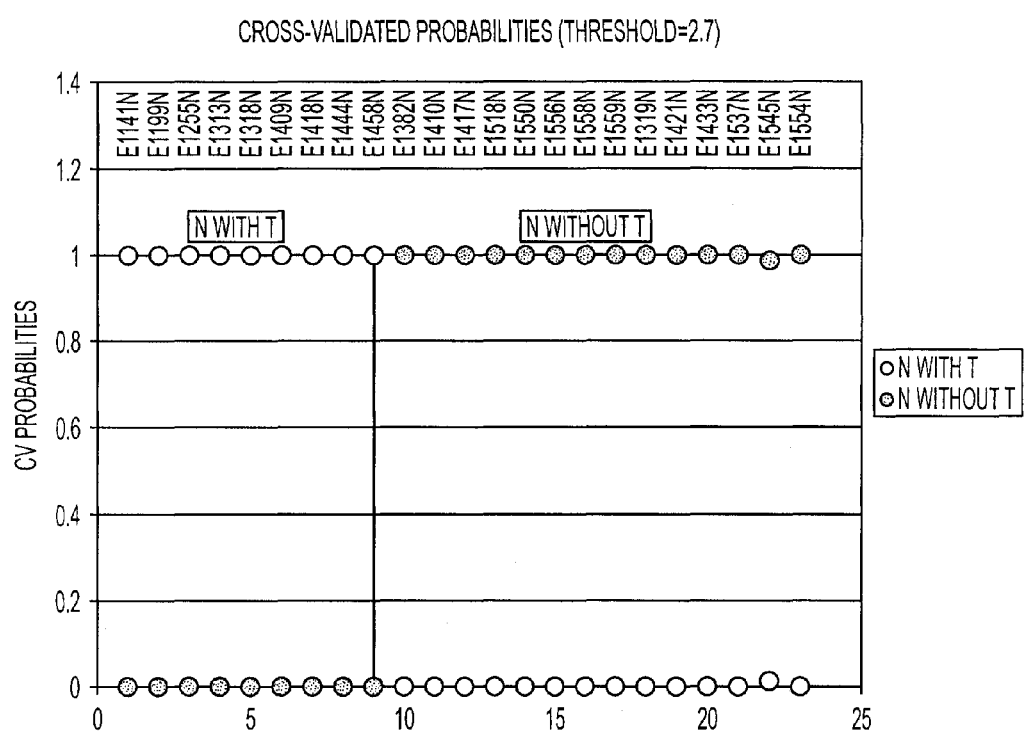
FIG. 1 shows the predicted diagnoses in comparison of NE from EAC patients vs. patients with either BA only or no BA. Patients with EAC, to the left of and on the vertical line, were diagnosed correctly in every case, as were all control patients without any lesion (to the right of the vertical line). Top left and bottom right, likelihood of being an EAC patient; Bottom left and top right, likelihood of being a non-cancer patient.

The sequence listing includes the National Center for Biotechnology Information—Entrez Nucleotide database sequences for each of the genes set forth in Table 3.

DETAILED DESCRIPTION

The present invention is directed to methods for diagnosing esophageal cancer or predisposition to esophageal cancer in a subject based on gene expression patterns. Interestingly, the gene expression patterns of cancer patients and pre-cancer patients differ from normal even in the esophageal epithelial cells which appear morphologically normal. Thus selection of particular locations for biopsy is not necessary. Even if a lesion is not detected visually with an endoscope, an abnormality or a predisposition can be detected.

Much of the analysis of the present methods can be automated and calculated by computer. Identifying presence or predisposition to esophageal cancer can be accomplished for example by recording a result in a patient's chart, on a computer print out, delivered via telephone or email, whether by machine or human.

Diagnosing Cancer—Different Subjects

In particular, the present invention is directed to methods for diagnosing cancer in a subject comprising (a) determining a gene expression pattern of a biological sample from a subject, and (b) comparing the gene expression pattern of (a) with a gene expression pattern of a biological sample from a subject that does not have cancer, wherein when differential gene expression is detected, the subject is diagnosed as having cancer.

In these embodiment, the skilled artisan will understand that the methods can be used to diagnose cancer by comparing the gene expression pattern of a biological sample from a subject, such as a patient suspected of having a cancer, with the gene expression pattern from a second subject previously screened and determined not to have the particular cancer for which the first subject is being screened. Where there is a difference in the two gene expression patterns, a diagnosis of cancer may be made. The comparison may be conducted using shrunken nearest centroid predictors analysis.

While the present invention includes methods of diagnosis where the gene expression patterns are determined from biological samples from the same source material from two different subjects, the present invention includes methods of diagnosis where the biological samples may be from different source materials from the different subjects.

The methods may employ additional steps to confirm the diagnosis of cancer or predisposition, where such steps are any of those known by the skilled artisan to allow a diagnosis of cancer or confirmation of a diagnosis of cancer, including morphological and histological examinations, and screening for a particular cancer marker associated with the cancer for which the subject is being screened.

The present invention is thus directed to a method for diagnosing cancer in a subject comprising (a) determining a gene expression pattern of a biological sample from a subject, and (b) comparing the gene expression pattern of (a) with a gene expression pattern of a biological sample from a subject that does not have cancer using shrunken nearest centroid predictors, wherein when differential gene expression is detected, the subject is diagnosed as having cancer.

The present invention is also directed to a method for diagnosing esophageal adenocarcinoma in a subject comprising (a) determining a gene expression pattern of esophageal epithelium from a subject, and (b) comparing the gene expression pattern of (a) with a gene expression pattern of esophageal epithelium from a subject that does not have cancer, wherein when differential gene expression is detected, the subject is diagnosed as having esophageal adenocarcinoma.

The present invention is further directed to a method for diagnosing esophageal adenocarcinoma in a subject comprising (a) determining a gene expression pattern of esophageal epithelium from a subject, and (b) comparing the gene expression pattern of (a) with a gene expression pattern of esophageal epithelium from a subject that does not have cancer using shrunken nearest centroid predictors, wherein when differential gene expression is detected, the subject is diagnosed as having esophageal adenocarcinoma.

Comparisons to other subjects can be also be done by ascertaining expression values in populations of relevant individuals and determining the range of values of expression that occur in those populations. Thus, after such data has been collected and validated, absolute values can be determined in subjects and the absolute values can be compared to the data collected for relevant populations.

Diagnosing Cancer—Same Subject

In a variation on the methods of the present invention discussed above, the present invention is also directed to methods for diagnosing cancer in a subject comprising (a) determining a gene expression pattern of a first biological sample from a subject, and (b) comparing the gene expression pattern of (a) with a gene expression pattern of a second biological sample from the subject, wherein when differential gene expression is detected, the subject is diagnosed as having cancer.

In these embodiments, the skilled artisan will understand that the methods can be used to diagnose cancer by comparing the gene expression pattern of two different biological samples obtained from the subject. For example, and as discussed further herein, cancer may be diagnosed in a subject that exhibits no symptoms of disease by comparing gene expression patterns in biological samples obtained from different regions of the same tissue or obtained from different regions of the body, or by comparing gene expression patterns in biological samples obtained from different source material from the same subject. While the two samples may be selected from regions of the same tissue that have no gross morphological differences, the two sample may also be selected from regions of the same tissue that exhibit some morphological differences. For example, morphological differences may include swelling, differences in color, such as redness, differences in surface architecture, differences in mucosal layers, and differences in moisture content.

The comparison may be conducted using shrunken nearest centroid predictors analysis. Where there is a difference in the two gene expression patterns, a diagnosis of cancer may be made. The method may include additional steps to confirm the diagnosis of cancer, where such steps are any of those known by the skilled artisan to allow a diagnosis of cancer or confirmation of a diagnosis of cancer, including morphological and histological examinations, and screening for a particular cancer marker associated with the cancer for which the subject is being screened.

Accordingly, the present invention is directed to a method for diagnosing cancer in a subject comprising (a) determining a gene expression pattern of a first biological sample from a subject, and (b) comparing the gene expression pattern of (a) with a gene expression pattern of a second biological sample from the subject using shrunken nearest centroid predictors, wherein when differential gene expression is detected, the subject is diagnosed as having cancer.

The present invention is directed to a method for diagnosing esophageal adenocarcinoma in a subject comprising (a) determining a gene expression pattern of a first sample of esophageal epithelium from a subject, and (b) comparing the gene expression pattern of (a) with a gene expression pattern of a second sample of esophageal epithelium from the subject, wherein when differential gene expression is detected, the subject is diagnosed as having esophageal adenocarcinoma.

The present invention is directed to a method for diagnosing esophageal adenocarcinoma in a subject comprising (a) determining a gene expression pattern of a first sample of esophageal epithelium from a subject, and (b) comparing the gene expression pattern of (a) with a gene expression pattern of a second sample of esophageal epithelium from the subject using shrunken nearest centroid predictors, wherein when differential gene expression is detected, the subject is diagnosed as having esophageal adenocarcinoma.

The present invention is directed to a method for diagnosing cancer in a subject comprising (a) determining a gene expression pattern of a first biological sample from a subject, and (b) comparing the gene expression pattern of (a) with a gene expression pattern of a second biological sample from the subject using shrunken nearest centroid predictors, wherein when differential gene expression is detected, the subject is diagnosed as having cancer, and wherein the locations from which the first and second biological samples are obtained are separated by a distance of at least 3 cm in said subject.

The present invention is directed to a method for diagnosing esophageal adenocarcinoma in a subject comprising (a) determining a gene expression pattern of a first sample of esophageal epithelium from a subject, and (b) comparing the gene expression pattern of (a) with a gene expression pattern of a second sample of esophageal epithelium from the subject, wherein when differential gene expression is detected, the subject is diagnosed as having esophageal adenocarcinoma, and wherein the locations from which the first and second biological samples are obtained from the esophageal epithelium are separated by a distance of at least 3 cm in said subject.

The present invention is directed to a method for diagnosing esophageal adenocarcinoma in a subject comprising (a) determining a gene expression pattern of a first sample of esophageal epithelium from a subject, and (b) comparing the gene expression pattern of (a) with a gene expression pattern of a second sample of esophageal epithelium from the subject using shrunken nearest centroid predictors, wherein when differential gene expression is detected, the subject is diagnosed as having esophageal adenocarcinoma, and wherein the locations from which the first and second biological samples are obtained from the esophageal epithelium are separated by a distance of at least 3 cm in said subject.

The present invention is directed to a method for diagnosing cancer in a subject comprising (a) determining a gene expression pattern of a first biological sample from a subject, and (b) comparing the gene expression pattern of (a) with a gene expression pattern of a second biological sample from the subject using shrunken nearest centroid predictors, wherein when differential gene expression is detected, the subject is diagnosed as having cancer, and wherein the locations from which the first and second biological samples are obtained have a grossly different appearance.

The present invention is directed to a method for diagnosing esophageal adenocarcinoma in a subject comprising (a) determining a gene expression pattern of a first sample of esophageal epithelium from a subject, and (b) comparing the gene expression pattern of (a) with a gene expression pattern of a second sample of esophageal epithelium from the subject, wherein when differential gene expression is detected, the subject is diagnosed as having esophageal adenocarcinoma, and wherein the locations from which the first and second biological samples are obtained from the esophageal epithelium have a grossly different appearance.

The present invention is directed to a method for diagnosing esophageal adenocarcinoma in a subject comprising (a) determining a gene expression pattern of a first sample of esophageal epithelium from a subject, and (b) comparing the gene expression pattern of (a) with a gene expression pattern of a second sample of esophageal epithelium from the subject using shrunken nearest centroid predictors, wherein when differential gene expression is detected, the subject is diagnosed as having esophageal adenocarcinoma, and wherein the locations from which the first and second biological samples are obtained from the esophageal epithelium have a grossly different appearance.

Detecting Differential Gene Expression

The present invention also includes methods for detecting differential gene expression in a subject comprising (a) determining a gene expression pattern of a biological sample from a subject, and (b) comparing the gene expression pattern of (a) with a pre-determined gene expression pattern, wherein when the gene expression pattern of (a) is different from the pre-determined gene expression pattern, differential gene expression is detected.

These methods can be used to screen for differences in gene expression patterns between individuals, differences in gene expression patterns between different biological samples obtained from the same subject, or differences in gene expression patterns over time found in biological samples obtained from the same source material within a subject. These methods can be used to identify one specific gene, or more than one gene. The comparison may be conducted using shrunken nearest centroid predictors analysis. Where there is a difference in the two gene expression patterns, a diagnosis of cancer may be made. The method may include additional steps to confirm the diagnosis of cancer, where such steps are any of those known by the skilled artisan to allow a diagnosis of cancer or confirmation of a diagnosis of cancer, including morphological and histological examinations, and screening for a particular cancer marker associated with the cancer for which the subject is being screened.

Where there is a difference in the two gene expression patterns, the methods may include additional steps to confirm that the gene or genes identified can be used as cancer markers. Further steps may also be included to identify the gene or genes found using these methods.

Similarly, where there is a difference in the two gene expression patterns, a prediction can be made that the subject will develop cancer or that the subject has an increased risk for developing cancer. As used herein, an increased risk for developing cancer means that the subject has a risk for developing a particular cancer that is greater that the risk for developing that particular cancer in the population as a whole. As used herein, the population as a whole may mean individuals sharing the same sex, age range, physical health, medical condition, or geographic location. For example, the population as a whole may mean adult humans residing in the United States.

Accordingly, the present invention is directed to a method for detecting differential gene expression in a subject comprising (a) determining a gene expression pattern of a biological sample from a subject, and (b) comparing the gene expression pattern of (a) with a pre-determined gene expression pattern using shrunken nearest centroid predictors, wherein when the gene expression pattern of (a) is different from the pre-determined gene expression pattern, differential gene expression is detected.

The present invention is also directed to a method for detecting differential gene expression in a subject comprising (a) determining a gene expression pattern of esophageal epithelium from a subject, and (b) comparing the gene expression pattern of (a) with a pre-determined gene expression pattern of esophageal epithelium, wherein when the gene expression pattern of (a) is different from the pre-determined gene expression pattern, differential gene expression is detected.

The present invention is also directed to a method for detecting differential gene expression in a subject comprising (a) determining a gene expression pattern of esophageal epithelium from a subject, and (b) comparing the gene expression pattern of (a) with a pre-determined gene expression pattern of esophageal epithelium using shrunken nearest centroid predictors, wherein when the gene expression pattern of (a) is different from the pre-determined gene expression pattern, differential gene expression is detected.

Diagnosing Cancer Using Markers

In a further variation, the present invention is directed to methods for diagnosing cancer in a subject comprising (a) determining an expression pattern of one or more genes in a biological sample from a subject, and (b) comparing the expression pattern of (a) with an expression pattern of the one or more genes in a biological sample from a subject that does not have cancer, wherein when differential gene expression is detected, the subject is diagnosed as having cancer.

As discussed herein, differential gene expression can be used to diagnosis cancer in a subject by comparing the expression level of one or more genes in a subject, such as a patient suspected of having cancer, with the expression level of one or more genes from a subject that is known not to have cancer. One or more specific genes may be used that have previously been shown to be correlated with a specific cancer.

These methods can be used to screen for differences in gene expression patterns between individuals, differences in gene expression patterns between different biological samples obtained from the same subject, or differences in gene expression patterns over time found in biological samples obtained from the same source material within a subject.

The comparison may be conducted using shrunken nearest centroid predictors analysis. Where there is a difference in the two gene expression patterns, a diagnosis of cancer may be made. The method may include additional steps to confirm the diagnosis of cancer, where such steps are any of those known by the skilled artisan to allow a diagnosis of cancer or confirmation of a diagnosis of cancer, including morphological and histological examinations, and screening for a particular cancer marker associated with the cancer for which the subject is being screened.

Similarly, where there is a difference in the two gene expression patterns, a prediction can be made that the subject will develop cancer or that the subject has an increased risk for developing cancer. As used herein, an increased risk for developing cancer means that the subject has a risk for developing a particular cancer that is greater that the risk for developing that particular cancer in the population as a whole. As used herein, the population as a whole may mean individuals sharing the same sex, age range, physical health, medical condition, or geographic location. For example, the population as a whole may mean adult humans residing in the United States.

The one or more genes used in the determination of an expression pattern may be any of those set forth in Table 1, or the subset shown in Table 2. The National Center for Biotechnology Information—Entrez Nucleotide sequences for each of the genes set forth in Table 3 are included in the Sequence Listing. Other genes in Tables 1 and 2 can be used with the sequence data that are present in the NCBI database, which are expressly incorporated herein with the sequences present as of the priority date of this application.

Accordingly, the present invention is directed to a method for diagnosing cancer in a subject comprising (a) determining an expression pattern of one or more genes in a biological sample from a subject, and (b) comparing the expression pattern of (a) with an expression pattern of the one or more genes in a biological sample from a subject that does not have cancer using shrunken nearest centroid predictors, wherein when differential gene expression is detected, the subject is diagnosed as having cancer.

The present invention is directed to a method for diagnosing esophageal adenocarcinoma in a subject comprising (a) determining an expression pattern of one or more genes in esophageal epithelium from a subject, and (b) comparing the expression pattern of (a) with an expression pattern of the one or more genes in esophageal epithelium from a subject that does not have esophageal adenocarcinoma, wherein when differential gene expression is detected, the subject is diagnosed as having esophageal adenocarcinoma.

The present invention is directed to a method for diagnosing esophageal adenocarcinoma in a subject comprising (a) determining an expression pattern of one or more genes in esophageal epithelium from a subject, and (b) comparing the expression pattern of (a) with an expression pattern of the one or more genes in esophageal epithelium from a subject that does not have esophageal adenocarcinoma using shrunken nearest centroid predictors, wherein when differential gene expression is detected, the subject is diagnosed as having esophageal adenocarcinoma.

The present invention is also directed to a method for diagnosing esophageal adenocarcinoma in a subject comprising (a) determining an expression pattern of one or more genes in esophageal epithelium from a subject, and (b) comparing the expression pattern of (a) with an expression pattern of the one or more genes in esophageal epithelium from a subject that does not have esophageal adenocarcinoma, wherein when differential gene expression is detected, the subject is diagnosed as having esophageal adenocarcinoma, and wherein the one or more genes are genes selected from Table 1.

The present invention is also directed to a method for diagnosing esophageal adenocarcinoma in a subject comprising (a) determining an expression pattern of one or more genes in esophageal epithelium from a subject, and (b) comparing the expression pattern of (a) with an expression pattern of the one or more genes in esophageal epithelium from a subject that does not have esophageal adenocarcinoma using shrunken nearest centroid predictors, wherein when differential gene expression is detected, the subject is diagnosed as having esophageal adenocarcinoma, and wherein the one or more genes are genes selected from Table 1.

The present invention is also directed to a method for diagnosing esophageal adenocarcinoma in a subject comprising (a) determining an expression pattern of one or more genes in esophageal epithelium from a subject, and (b) comparing the expression pattern of (a) with an expression pattern of the one or more genes in esophageal epithelium from a subject that does not have esophageal adenocarcinoma, wherein when differential gene expression is detected, the subject is diagnosed as having esophageal adenocarcinoma, and wherein the one or more genes are genes selected from Table 2.

The present invention is also directed to a method for diagnosing esophageal adenocarcinoma in a subject comprising (a) determining an expression pattern of one or more genes in esophageal epithelium from a subject, and (b) comparing the expression pattern of (a) with an expression pattern of the one or more genes in esophageal epithelium from a subject that does not have esophageal adenocarcinoma using shrunken nearest centroid predictors, wherein when differential gene expression is detected, the subject is diagnosed as having esophageal adenocarcinoma, and wherein the one or more genes are genes selected from Table 2.

In an embodiment, an expression pattern of at least 1, 2, 3, 4, 5, 6, 7, 8, 9, 10, 11, 12, 13, 14, 15, 16, 17, 18, 19, 20, 21, 22 or all 23 of the genes of Table 1 is determined. In a further embodiment, the expression pattern of at least 1, 2, 3, 4, 5, 6, 7, 8, 9, 10, 11, 12, 13, 14, 15, 16 or all 17 of the genes of Table 2 is determined. The number to be determined is that number which gives sufficient sensitivity and specificity. The number to be determined is that number which gives an acceptable number of false positives and acceptable number of false negatives.

Diagnoses and prognoses determined using the subject methods can be confirmed and combined with other means of assessment. These include physical findings, radiological findings, pH determinations, endoscopic determinations, pathological determinations, patient reports of symptoms, and the like.

In relevant embodiments of the present invention the skilled artisan will understand the identity of the particular cancer being diagnosed need not be limited, and may include adenocarcinoma, squamous cell cancer, leukemia, lymphoma, melanoma, myeloma, sarcoma, teratocarcinoma, and cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In some embodiments the cancer is esophageal cancer, adenocarcinoma or squamous cell cancer.

Similarly, the identity of the subject to which the methods of the present invention are applied is not limited. However, in some embodiments, the subject is a bird or a mammal. For example, the subject may be a dog, cat, horse, simian or human.

The gene expression pattern may be determined by any method know in the art, although the pattern is typically determined using a polynucleotide microarray as described herein. In some embodiments, the gene expression patterns are analyzed and/or compared by shrunken nearest centroid predictors (SNCP). Detailed means for such analysis and/or comparison using shrunken nearest centroid predictors is provided in herein, and is based on an adaptation of classical nearest centroids prediction analysis, tailored specifically to microarray data (Tibshirani et al., *Proc Natl Acad Sci USA* 99(10):6567-72 (2002)). Permutation analysis, as also described herein, may be used in conjunction with the SNCP analysis.

For each new specimen, we calculate the square distance to the normal centroid and the square distance to the cancer centroid. The centroid (normal or cancer) to which the specimen is closest, in squared distance, defines the predicted class for that new sample.

As an example, if we have a new specimen, we would determine the level of the 11 genes in the centroid. Let these levels be G1, G2, ... G11. We already have the centroid values for each of the 11 genes for the normal class and for the cancer class. Let these be CN1, CN2, ... CN11 and CC1, CC2, ..., CC11. The score of the new specimen for the normal class would be calculated as:

Score for normal $SN=(G1-CN1)^2+(G2-CN2)^2+\ldots+(G11-CN11)^2$ and, the score of the new specimen for the cancer class would be calculated as:

Score for cancer $SC=(G1-CC1)^2+(G2-CC2)^2+\ldots+(G11-CC11)^2$.

If $SN>SC$, then the specimen is classified as cancer. If $SN<SC$ then the specimen is classified as normal.

The biological sample tested in the methods of the present invention may be any biological sample from which polynucleotides or proteins may be obtained. In particular, the biological sample is one that contains cells or cellular material, proteins or polynucleotides. For example, the biological sample may be a biological fluid, such as lymph, serum, plasma, whole blood, urine, synovial fluid and spinal fluid; a cell type, such as bone marrow, immune, keratinocytes, epithelial cells, hepatocytes, renal cells, breast tissue cells, bladder cells, prostate cells, pancreatic cells; a tissue, such as skin, muscle, liver, kidney, pancreas, heart, lung, breast, male or reproductive organs, lymphatic system, nervous system, digestive system, bladder, colon, connective tissue, where the tissue may be normal, cancerous or wounded tissue; or biopsies. In some embodiments, the biological sample is mucosa, esophageal epithelium, or squamous esophageal epithelium. In one embodiment, the biological sample is tissue diagnosed as Barrett's esophagus. Samples can be collected by endoscopy, or other collecting means, including surgical spatulas, sponges, balloons, esophageal brush-capsule. See Cancer Cytopathol. 2000; 90:10-6; see also Cancer. 1997; 80(11): 2047-59. Some of these may be used in conjunction with endoscopy and some may be used independently.

As indicated further throughout this application, one of the advantages of the methods disclosed herein pertains to the ability to analyze morphologically-normal tissue, and to thereby diagnose cancer early based on the gene pattern. This is important for at least two reasons: (1) the assumption that disease progression is minimal in morphologically-normal tissue and treatment can thus begin prior to major damage to biological tissues and systems; and (2) diagnosticians do not need to first locate morphologically-abnormal tissue and analyze such tissue for gene expression. With regard to esophageal adenocarcinoma and squamous cell cancer, cancerous lesions can be especially difficult to find. The methods herein thus allow for an accurate analysis and diagnosis based on pre-cancerous tissue or tissue that may be some distance from cancerous tissue.

Therefore, in some embodiments, the biological sample has a morphologically-normal appearance. In some embodiments, the biological sample is morphologically-normal appearing esophageal epithelium, or morphologically-normal appearing squamous esophageal epithelium.

The methods of the present invention may be practiced using polynucleotides or proteins obtained directly from biological samples, or using polynucleotides or proteins produced from or amplified from polynucleotides obtained directly from biological samples. For example, cDNA may be isolated from a biological sample, and then PCR conducted to amplify the cDNA to obtain a sufficient amount of a polynucleotide for use in the methods. mRNA may also be amplified as detailed below. Protein can be made using in vitro transcription/translation systems, which are well known in the art.

While the location from which the biological samples are taken is not critical, they should be at a sufficient distance apart to be separate samples. When there is a morphological difference, the samples can be taken from those regions of the source material, such as a tissue, that have different morphological appearances. In general, the leading edges of these samples should be at a distance of at least 1, 2, 3, 4, 5, 6, 7, 8, 9, 10, 15, 20, 25 or 30 cm apart. When there is no morphological difference, the leading edges of the samples should be at a distance apart of at least 1, 2, 3, 4, 5, 6, 7, 8, 9, 10, 15, 20, 25 or 30 cm, such as when taken from the same tissue. The sample may also be collected from different regions of the body, such as where the sample is a bodily fluid. In an embodiment, the locations from which the first and second samples are obtained from a biological tissue are separated by a distance of at least 3 cm.

The gene expression patterns that are determined and compared in the methods of the present invention can be quantitative and/or qualitative patterns. For example, differential gene expression patterns can be based on the level at which the one or more genes are being expressed, and/or based on whether the one or more genes are being expressed at all. When the level of gene expression is determined and compared, a statistically significant difference may be used to demonstrate a difference in gene expression.

Solid supports according to the invention can be any substrate to which antibodies or oligonucleotide probes can be attached, either directly or indirectly through linker groups. Typically each species of antibody or species of oligonucleotide probe is located as a discrete geographic location on the substrate. Alternatively, each species of antibody or probe can be otherwise distinguishable, for example, based on a detectable label or other physical property. In one embodiment each species can be bound to a bead and the beads can be separated on the basis of size, magnetic characteristic, fluorescence spectrum, etc. Beads can also be used in discrete geographical locations, such as in wells of a microtiter plate. Solid supports are typically inert materials, such as glass, plastic, polymer, etc. They may be fabricated into sheets, strips plates, multi-well plates, beads, fabrics, etc. Solid supports typically have probes/antibodies for only a small subset of the entire genome or proteome. Aside from controls and standards, only probes or antibodies for genes which are found to be relevant to esophageal disease need be present. Thus the probes or antibodies for assessing expression of the genes in Table 3 may comprise at least 5%, at least 10%, at least 25%, at least 50%, at least 75%, at least 90% of the probes or antibodies on the solid support. Expression of any number of relevant genes can be tested including 1, 2, 3, 4, 5, 6, 7, 8, 9, 10, or 11 of the genes listed in Table 3.

EXAMPLES

The following embodiments are merely exemplary and are not intended to be limiting.

Patients and Tissues

Six patients with BA alone, nine with BA and concomitant EAC, and eight with neither BA nor EAC were included in this study. The eight patients without BA or EAC had had endoscopy for unrelated indications, such as peptic ulcer disease, but had undergone endoscopic biopsy of the gastroesophageal junction that was histologically normal. In all cases, biopsies from grossly normal-appearing squamous esophageal epithelium at least 7 cm proximal to the upper limit of the Barrett's mucosa were included in the study. None of the patients with BA alone had concomitant dysplasia. Fresh NE (normal esophagus) biopsy specimens were immediately frozen and stored in liquid nitrogen until further use. Matching morphologic controls were obtained from the same sites as the research specimens and were examined by hematoxylin and eosin staining by an expert gastrointestinal pathologist at the University of Maryland. Informed consent was obtained from all patients under an institutionally approved research protocol.

Location of the Normal Squamous Esophageal Biopsies

The normal squamous esophagus (NE) areas biopsied were grossly normal, without any endoscopic evidence of esophagitis or reflux changes. In patients with obvious mass lesions in their esophagus, biopsies were obtained at least 7 cm proximal to these lesions. Similarly, biopsies from BA patients were performed at least 7 cm away from the area that showed endoscopic evidence of Barrett's esophagus. In patients lacking BA or EAC, biopsies were performed from areas that did not show any gross endoscopic abnormalities. Finally, all NE specimens were analyzed histologically, and there was no evidence of any metaplasia or other changes found in any of these NE samples.

cDNA Microarray Production and Hybridization

Detailed protocols for glass slide coating, cDNA clone preparation and verification, microarray printing, post-printing slide processing, RNA extraction, RNA amplification, labeling and hybridization were performed as previously described (Selaru et al., *Oncogene* 21(3):475-8 (2002); Zou et al., *Oncogene* 21(31):4855-62 (2002); Xu et al., *Cancer Res* 62(12):3493-7 (2002)).

RNA Extraction, Amplification, and Labeling of the aRNA Probe

Total RNA (3-20 µg) was extracted from freshly frozen tissue using an RNeasy kit (Quiagen, Valencia, Calif.) and amplified using the AmpliScript T7-flash transcription kit (Epicentre, Madison, Wis.). Labeling was performed on 6 µg of aRNA by incorporating Cy3- or Cy5-labeled dCTP using random primers and Superscript reverse transcriptase (Xu et al., *Cancer Res* 62(12):3493-7 (2002)). The resulting probes were purified with a Microcon microcentrifuge filter device and recovered in a volume of 25 The reference probe was prepared from an equimolar mixture containing aRNAs from eight human malignant cell lines, as described previously. Microarray preparation was performed as described (Selaru et al., *Oncogene* 21(3):475-8 (2002); Mori et al., *Cancer Res* 63(15):4577-82 (2003); Xu et al., *Cancer Res* 62(12):3493-7 (2002)).

Microarray Normalization

An algorithm for normalizing microarray data was adapted that improves its accuracy and dynamic range (Yang et al., *Nucleic Acids Res* 30(4):e15 (2002)). Both within-slide and inter-slide normalization were accomplished. In this fashion, local distortions in signal and background intensity within different regions of a slide, as well as overall differences in hybridization or labeling efficiencies between slides, were overcome. It was determined that the within-slide normalization performed optimally when 4 blocks were used as the normalization unit (each block being produced by a different microarray pin). It was assumed that each group of 4 blocks was equivalent in average signal intensity and range to the next group of 4 blocks on the array. Thus, 8 normalization units per slide were utilized. This assumption was based on an optimization strategy in which groups of 1, 2, 4, 8, and 16 blocks were tested as the normalization unit, which showed that the 4-block unit performed with the least inaccuracy when a random number generator was used to produce the 8,064 values on a microarray slide (data not shown). Thus, this normalization method (Yang et al., *Nucleic Acids Res* 30(4):e15 (2002)) consisted of three steps: intensity-dependent normalization within each slide, scale normalization within each slide, and inter-slide normalization.

Shrunken Nearest Centroid Predictor (SNCP) Model

The Shrunken nearest centroid predictor (SNCP) model was analyzed to determine if it could be used to identify gene expression patterns or individual genes as biomarkers to distinguish between the normal esophagus of patients with, vs. without, accompanying EAC. SNCPs discovered both broad patterns and individual genes that were highly accurate in their ability to identify whether or not a patient had accompanying remotely located cancer.

The SNCP method is an adaptation of classical nearest centroids prediction analysis, tailored specifically to microarray data (Tibshirani et al., *Proc Nall Acad Sci USA* 99(10): 6567-72 (2002)). Each centroid is comprised of weighted averages of genes (elements) on the microarray for a particular diagnostic category, or "class." Thus, the centroids each contain 8,064 elements, since there are 8,064 genes on each microarray. Gene weighting is directly proportional to the raw average expression value, but inversely proportional to the standard deviation (i.e., the variability) of expression value within a given class. Centroids are then shrunken by adjusting the threshold value, which removes genes with lower weighted averages (thus yielding a smaller set of relevant genes). Gene expression variations below a certain threshold value are made equal to zero and ignored. Thus, shrinkage consists of moving the centroid towards zero by threshold, and setting it equal to zero when it drops completely (Tibshirani et al., *Proc Natl Acad Sci USA* 99(10): 6567-72 (2002)).

The choice of Δ (amount of shrinkage) is dependent upon two variables: 1. prediction error minimization; 2. the number of genes that are left in the model. More specifically, when all the genes on the microarrays are used, the prediction error is significant. During the process of data fitting, the SNCP model excludes outliers, i.e., genes that are not usable for the prediction. It is, however, possible to achieve the minimum prediction error for a range of Δs. In this particular case, the model can predict the predefined categories using a variable number of genes. Under these conditions, the smaller the Δ, the higher the number of genes left in the model, and vice versa.

Internal validation of results is performed using cross-validation. The value of K (fold cross-validation number) is set by default at 10; therefore, a 10-fold cross-validation was performed. In this 10-fold cross-validation, the specimens were randomly assigned to 10 groups. Nine of the ten groups were used for training, while the prediction is made on the 10th group. This procedure is repeated 10 times. For example, in the Normal-Normal versus Normal-Cancer comparison, training is done on 16 specimens, and then the model predicts the 17th specimen.

Permutation Analysis

SNCPs are mathematical models that learn by example. In other words, SNCPs identify a centroid for every group in the comparison. New specimens are classified by calculating the distance between the new specimen and each of the centroids. The specimen is classified into the class whose centroid is closest to the specimen. Ideally, the SNCPs should be tested on a test set, composed of specimens that were not used during training. This, however, may prove difficult when a small number of specimens are available for the study. One method to circumvent the need for a test set, while ensuring statistical significance is permutation analysis.

Permutation analysis is a statistical technique used to calculate the chances of obtaining classification results purely by chance. The analysis consists of randomly permuting the specimen labels and constructing classifiers (SNCPs) to categorize the specimens. In the current study, permutation resulted in randomly assigning specimens to one of two categories: N-N (NE specimens from patients lacking EAC or BA) and BA-CA (NE specimens from patients with Barrett's esophagus and concomitant esophageal adenocarcinoma). The SNCP model with the lowest prediction error was subsequently chosen. This procedure was repeated 100 times. In all 100 random permutations, SNCPs were unable to learn the two categories correctly (with an error=0). The mean group error for the 100 permutations was 0.36. This finding demonstrated that the possibility that the SNCP learned the two categories (N-N and BA-CA) correctly by chance alone was less than 1 in 100.

Experiment 1

In the initial application of the methodology described above, NE biopsy specimens of both subjects with completely normal esophagi (Normal-Normal, or N-N) and patients with BA but without EAC (BA-alone) were considered together as a single group, which was compared to NE biopsy specimens of patients with Barrett's esophagus with concomitant EAC (BA-CA). Centroids were 100% accurate in predicting which subject or patient was in which group in this comparison, as shown in FIG. 1. A list containing 195 genes was generated, based on their differential expression between normal esophagi from normal patients and normal esophagi from patients with EAC. Table 3 contains a few of these genes, with already known links to cancer.

Experiment 2

Figure 2:
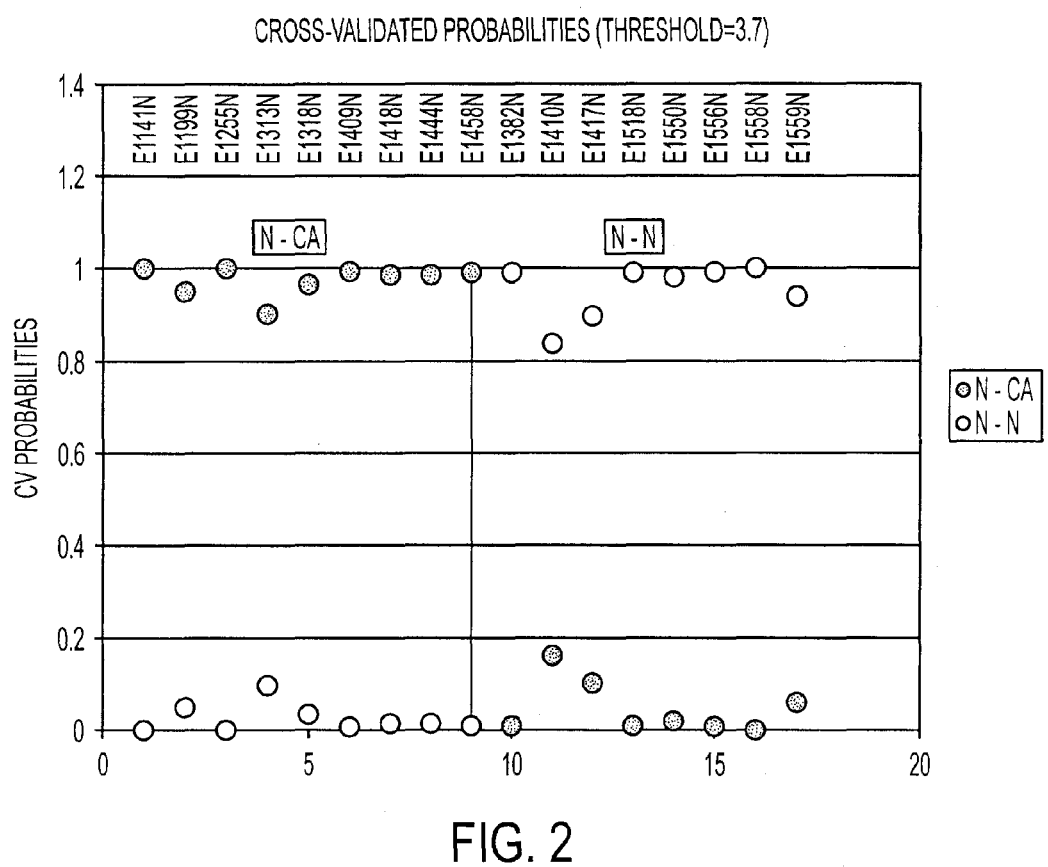
FIG. 2 shows the predicted diagnoses in comparison of NE from EAC patients vs. P control subjects (patients with neither BA nor EAC). Patients with EAC, to the left of the vertical line, were diagnosed correctly in every case, as were all control subjects patients without any lesion (to the right of the vertical line). Bottom left and top right, likelihood of being a control subject; top left and bottom right, likelihood of being an EAC patient.

In an effort to further narrow the number of variables involved in the difference between NE biopsies from patients with concomitant EAC vs. subjects without EAC, NE from subjects without esophageal disease vs. NE from EAC patients only (i.e., excluding noncancer subjects with BA) was also compared. This comparison revealed the accuracy of centroids in distinguishing these two subgroups, as shown in FIG. 2.

Experiment 3

Figure 3:
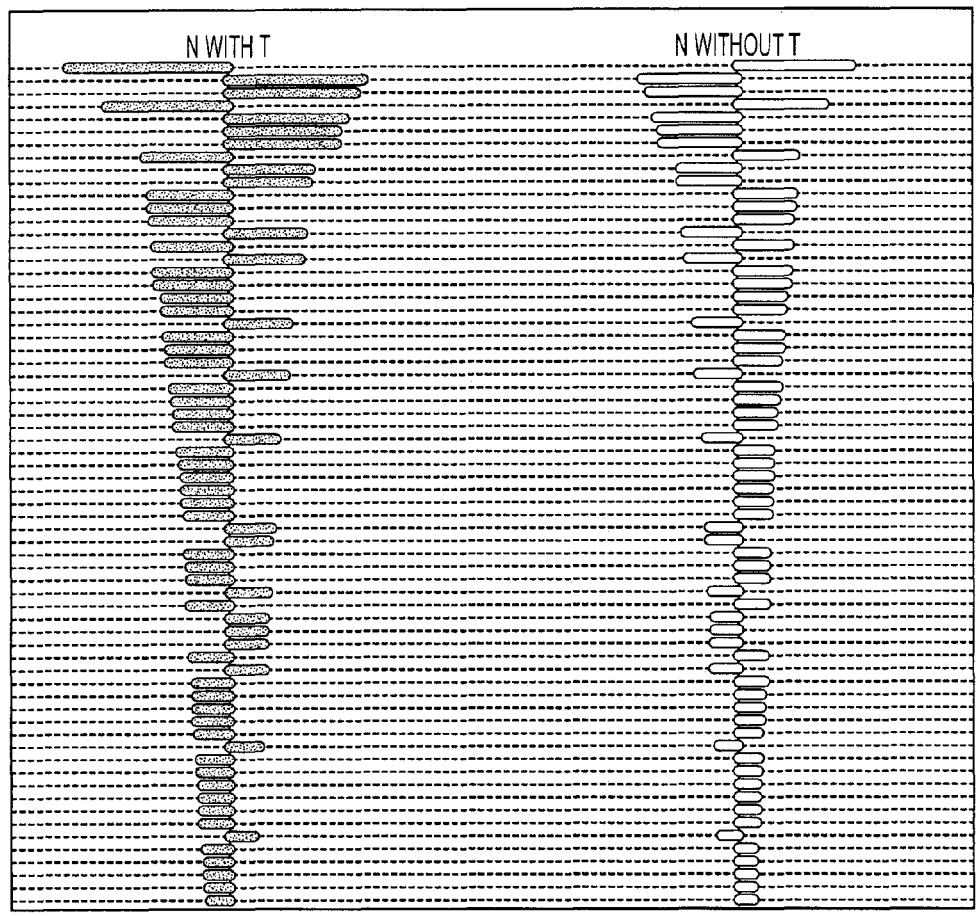
FIG. 3 shows over-expressed genes designated by rightward-extending bars; those that are under-expressed protrude to the left. Left centroid, NE specimens from subjects with EAC; right centroid, NE from patients without EAC. This plot demonstrates that genes under-expressed in non-cancer patients are over-expressed in EAC patients, and vice versa. SNCP threshold=2.7.

The SNCPs also generated visual displays of centroids, showing which genes were over-expressed and which were under-expressed in NE from patients with vs. those without accompanying EAC. The genes in these displays are arrayed in order of decreasing differential expression, with the most differentially expressed genes at the top and the least differentially expressed genes at the bottom. One such typical centroid is displayed in FIG. 3.

Genes represented in a shrunken centroid derived by comparing NE tissues between cancer and non-cancer patients are shown in Table 3. Among them are many genes with previous links to esophageal cancer or to cancers in general: histone biomarkers, gravin, HLA-DRA, keratin 8 (KRT8), glutathione peroxidase 2 (GPX2), the mitotic checkpoint protein kinase BUB1B, the progestin-induced protein DD5 and transglutaminase 3.

TABLE 3

| Gene ID | Gene Name | N with T | N without T |
|---|---|---|---|
| AB003476 | gravin | −0.7322 | 0.4707 |
| NM_005319 | H1 histone family, member 2 (H1F2) | 0.5907 | −0.3797 |
| XM_004416 | H2A histone family, member L (H2AFL) | 0.5384 | −0.3461 |
| NM_003519 | H2B histone family, member C (H2BFC) | 0.5062 | −0.3254 |
| NM_002273 | keratin 8 (KRT8) | 0.3834 | −0.2465 |
| NM_015902 | progestin induced protein (DD5) | −0.3112 | 0.2001 |
| NM_003516 | H2A histone family, member O (H2AFO) | 0.2322 | −0.1493 |
| XM_009572 | transglutaminase 3 (TGM3) | −0.2078 | 0.1336 |
| NM_019111 | major histocompatibility complex, class II, DR alpha (HLA-DRA) | 0.1695 | −0.109 |
| AF107297 | mitotic checkpoint protein kinase BUB1B (BUB1B) | −0.0626 | 0.0402 |
| NM_002083 | glutathione peroxidase 2 (gastrointestinal) (GPX2) | 0.0614 | −0.0395 |

Selected genes identified by comparison of NE from patients with EAC (N with T) vs. without EAC (N without T).
Threshold value set at 2.7;
N with T: gene score in the group of patients with esophageal adenocarcinoma;
N without T: gene score in the group of patients without esophageal adenocarcinoma.
Gene identifiers and gene names are shown in the two leftmost columns.

Previous studies have compared gene expression patterns among normal, metaplastic, and cancerous esophageal epithelia (Selaru et al., Oncogene 21(3):475-8 (2002); Xu et al., Cancer Res 62(12):3493-7 (2002), Guillem et al., Int J Cancer 88(6):856-61 (2000); Lu et al., Int J Cancer 91(3):288-94 (2001)). Moreover, a recent study by Wang, S et al., suggests that gene expression patterns in Barrett's esophagus are significantly closer to gene expression patterns in esophageal adenocarcinoma than to expression patterns in normal esophagus. This finding alarmingly implies that Barrett's esophagus is biologically closer to cancer than to normal esophagus (Wang et al., Oncogene 25(23):3346-56 (2006)). However, these studies have consisted of direct comparisons of these different types of esophageal epithelia to each other. In the current study, a different approach was undertaken: i.e., a comparison of the normal esophageal epithelia from patients at differing stages of esophageal neoplastic progression. This study found unique molecular signatures in normal esophageal epithelium that reflected concomitant neoplasia elsewhere in the esophagus.

The potential biologic ramifications of these results are far-reaching. The field effect found near esophageal tumors in surrounding normal epithelium has been well-described (Eads et al., Cancer Res 61(8):3410-8 (2001); Eads et al., Cancer Res 60(18):5021-6 (2000)). A recent study by Brabender et al. (Cancer Epidemiol Biomarkers Prev 14(9):2113-7 (2005)) identified a field effect by using a gene expression panel. In the current study, biopsies of normal esophagus were obtained at least 7 cm away from the tumor or Barrett's esophagus. The current findings suggest that esophageal cancer exerts a greater influence on the normal esophageal epithelium than previously known or suspected. While molecular alterations in histologically normal squamous esophageal epithelium have previously been described adjacent to cancers, the current findings suggest that alterations in gene expression and gene expression pattern accompanying cancer can affect large portions of the normal squamous esophagus. It was postulated that the development of esophageal adenocarcinoma is accompanied by widespread molecular phenotypic alterations that involve the entire normal squamous esophageal epithelium.

The present SNCP-based approach offers a number of advantages over other analytic techniques. These include the ability to differentiate among multiple specimen groups; the potential for rapid translation to the clinical setting; a low likelihood of over-fitting, yielding a low probability of erroneous diagnoses in new, independent datasets; and the capacity to yield a reduced number of diagnostic genes, which can themselves be developed as individual biomarkers as well as the basis for further molecular genetic studies (Tibshirani et al., Proc Nall Acad Sci USA 99(10):6567-72 (2002)).

In the current study, genes positioned the highest in centroids discriminating normal tissues from non-cancer vs. cancer patients were both interesting and relevant. For example, among the most highly ranked genes were members of the histone families (Table 3).

As single-gene predictors, histone biomarkers were accurate in distinguishing between accompanying cancer and its absence. Histones are basic nuclear proteins responsible for the nucleosome structure of chromosomal fibers in eukaryotes. Apart from promoter hypermethylation, modification of histone proteins is the second major component of epigenetic transcriptional control. DNA methylation and histone acetylation are integrally linked. Methylation is catalyzed by a family of DNA methyltransferases. DNA methyltransferases recruit histone deacetylases, leading to histone deacetylation and transcriptional repression. Methylated DNA is also recognized by a family of methylated DNA-binding proteins, which recruit histone deacetylases and ATP-dependent chromatin remodeling proteins, resulting in a tightly condensed chromatin structure and gene inactivation. Additional links between the "histone code" and the "cytosine methylation code" are increasingly evident (Johnstone et al., Nat Rev Drug Discov 1(4):287-99 (2002); Kouraklis et al., Curr Med Chem Anti-Canc Agents 2(4):477-84 (2002); Marks et al., Nat Rev Cancer 1(3):194-202 (2001)).

In addition, alterations of proteins in the histone acetyltransferase family (e.g., CREB-binding protein and p300) are associated with cancers of the breast, colon, liver, and hematopoietic system. Of particular relevance to the current findings, histone H4 is hyperacetylated in early stages of esophageal cancer cell invasion, and thereafter changes to a hypoacetylated state according to the degree of cancer progression (Toh et al., Oncol Rep 10(2):333-8 (2003)). These results suggest that a dynamic equilibrium between histone acetylase and deacetylase activities is disrupted in esophageal carcinogenesis, implying that an interaction may exist between hyperacetylation of histone H4 and histone deacetylase 1 expression (Toh et al., Oncol Rep 10(2):333-8 (2003)).

Similarly, by applying differential display to esophageal tumor and matched normal esophageal samples, histone H3.3 was identified among 49 cDNA ddPCR clones from esophageal cancers (ECs) (Graber et al., *Ann Surg Oncol* 3(2): 192-7 (1996)). Histone H3.3 was overexpressed in 4/6 ECs, but not in paired normal mucosa. Only 5/13 normal human cell lines from various organs, but 11/12 human cancer cell lines (including 9 of 9 adenocarcinoma lines) overexpressed 113.3 (Graber et al., *Ann Surg Oncol* 3(2):192-7 (1996)). Histones H3 and H4 were deacetylated in gastric cancer cell lines showing aberrant methylation of CHFR, a mitotic checkpoint gene, suggesting a role for histone deacetylation in methylation-dependent gene silencing (Satoh et al., *Cancer Res* 63(24):8606-13 (2003)).

Another gene identified in the current study was HLA-DRA. Major histocompatibility complex (MHC) molecules are of central importance in regulating the immune response against tumors. Loss of expression of HLA class II molecules on tumor cells affects the onset and modulation of the immune response through lack of activation of CD4+ T lymphocytes. In part, loss of expression is caused by mutations as shown for large B-cell lymphoma (Jordanova et al., *Immunogenetics* 55(4):203-9 (2003)). A recent study found downregulation of HLA-DRA in invasive cancers compared to dysplastic cervical lesions (Chil et al., *Acta Obstet Gynecol Scand* 82(12):1146-52 (2003)).

A strong predictive value of keratin 8 (KRT8) was also observed. KRT8 belongs to the intermediate filament family and associates with keratin 18 to form a heterotetramer of two type i and two type ii keratins. Its phosphorylation on serine residues is enhanced during EGF stimulation and mitosis. Dysregulation of keratin 8 is associated with esophageal carcinogenesis (Boch et al., *Gastroenterology* 112(3):760-5 (1997); Glickman et al., *Am J Surg Pathol* 25(5):569-78 (2001); Glickman et al., *Am J Surg Pathol* 25(1):87-94 (2001); Salo et al., *Ann Med* 28(4):305-9 (1996)).

Additional genes with known relevance to human cancer identified by this SNCP model included glutathione peroxidase 2 (GPX2), the mitotic checkpoint protein kinase BUB1B, and the progestin-induced protein DD5. As expected, BUB1B was expressed at high levels in the normal esophageal tissues of patients without cancer and underexpressed in patients with cancer. BUB1B is a component of the mitotic checkpoint that delays anaphase until all chromosomes are properly attached to the mitotic spindle. In BRCA2-deficient murine cells, BUB1 mutants potentiate growth and cellular transformation (Davenport et al., *Genomics* 55(1):113-7 (1999)). In addition, mutations in human BUB1B have demonstrated a dominant negative effect by disrupting the mitotic checkpoint when transfected into euploid colon cancer cell lines (Davenport et al., *Genomics* 55(1): 113-7 (1999)). Thus, BUB1B is a candidate tumor suppressor gene in the esophagus whose downregulation in normal esophageal tissue is associated with cancer development.

Transglutaminase 3, which was under-expressed in the normal tissue of tumor patients in this study, was recently found to be down-regulated in esophageal squamous cell carcinoma and head and neck squamous cell carcinoma by cDNA microarray studies comparing cancer and matching normal tissue (Luo et al., *Oncogene* 23(6):1291-9 (2004)).

In conclusion, the current study diagnosed patients with remote esophageal neoplasia based on biopsies of their remote normal epithelium alone, and provided a minimal list of genes necessary to do so. This proof-of-principle study establishes a theoretical basis to identify cancers in other organs by studying gene expression patterns or other molecular signatures in their matching normal epithelia. In addition, by shrinking the number of genes needed to arrive at a correct diagnosis, the current work showcases an approach to identify smaller numbers of genes worthy of further research from microarray data, both as biomarkers and for biologic or functional studies.

While the foregoing specification teaches the principles of the present invention, with examples provided for the purpose of illustration, it will be appreciated by one skilled in the art from reading this disclosure that various changes in form and detail can be made without departing from the true scope of the invention.

Each of the publications recited herein, including journal articles, books, manuals abstracts, posters, patents, and published patent applications, are hereby incorporated herein in their entireties.

We claim:

1. A method comprising:
    testing a sample of morphologically normal esophageal epithelial cells of a human subject and determining expression of one or more genes, wherein said one or more genes comprises gravin;
    determining a composite score of expression of the one or more genes;
    comparing the composite score to predetermined values for esophageal cancer or predetermined values for increased risk of esophageal cancer; and
    identifying the composite score as within the predetermined values for esophageal cancer or as within the predetermined values for increased risk of esophageal cancer if the composite score falls within the predetermined values.

2. A method comprising:
    testing a sample of esophageal epithelial cells of a human subject and determining expression of one or more genes selected from the group consisting of gravin; H1 histone family, member 2 (H1 F2); H2A histone family, member L (H2AFL); H2B histone family, member C (H2BFC); keratin 8 (KRT8); progestin induced protein (DD5); H2A histone family, member O (H2AFO); transglutaminase 3 (TGF3); major histocopatibility complex, class II, DR alpha (HLA-DRA); mitotic checkpoint protein kinase BUB1B (BUB1B); and glutathione peroxidase 2 (gastrointestinal) (GPX2), wherein said one or more genes comprises gravin;
    determining a composite score of expression of the one or more genes;
    comparing the composite score to predetermined values for esophageal cancer or increased risk of esophageal cancer; and
    identifying the composite score as within the predetermined values for esophageal cancer or predetermined values for increased risk of esophageal cancer if the composite score falls within the predetermined values.

3. A method comprising:
    testing a sample of morphologically normal esophageal epithelial cells of a human subject and determining expression of one or more genes selected from the group consisting of gravin; H1 histone family, member 2 (H1F2); H2A histone family, member L (H2AFL); H2B histone family, member C (H2BFC); keratin 8 (KRT8); progestin induced protein (DD5); H2A histone family, member O (H2AFO); transglutaminase 3 (TGF3); major histocompatibility complex, class II, DR alpha (HLA-DRA); mitotic checkpoint protein kinase BUB1B (BUB1B); and glutathione peroxidase 2 (gastrointestinal) (GPX2), wherein said one or more genes comprises gravin;
    determining a composite score of expression of the one or more genes;

comparing the composite score to predetermined values for esophageal cancer or increased risk of esophageal cancer; and identifying the composite score as within the predetermined values for esophageal cancer or increased risk of esophageal cancer if the composite score falls within the predetermined values.

4. The method of claim 1, 2, or 3 wherein mRNA expression of the one or more genes is determined.

5. The method of claim 1, 2, or 3 wherein protein expression of the one or more gene is determined.

6. The method of claim 2 or 3 wherein a composite score of expression of eleven genes is determined.

7. The method of claim 2 or 3 wherein a composite score of expression of ten genes is determined.

8. The method of claim 2 or 3 wherein a composite score of expression of nine genes is determined.

9. The method of claim 2 or 3 wherein a composite score of expression of eight genes is determined.

10. The method of claim 2 or 3 wherein a composite score of expression of seven genes is determined.

11. The method of claim 2 or 3 wherein a composite score of expression of six genes is determined.

12. The method of claim 2 or 3 wherein a composite score of expression of five genes is determined.

13. The method of claim 1, 2, or 3 wherein a diet that decreases risk of neoplasia is recommended when presence or increased risk of esophageal cancer is identified.

14. The method of claim 1, 2, or 3 wherein the sample is obtained by endoscopy.

15. The method of claim 1, 2, or 3 wherein the sample is obtained by an inflatable balloon.

16. The method of claim 1, 2, or 3 wherein the sample is obtained by a sponge.

17. The method of claim 1, 2, or 3 wherein the human subject has diagnosed Barrett's esophagus.

* * * * *

UNITED STATES PATENT AND TRADEMARK OFFICE
CERTIFICATE OF CORRECTION

PATENT NO.       : 8,679,759 B2                                  Page 1 of 1
APPLICATION NO. : 12/671406
DATED            : March 25, 2014
INVENTOR(S)      : Selaru et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 750 days.

Signed and Sealed this

Twenty-ninth Day of September, 2015

Michelle K. Lee
*Director of the United States Patent and Trademark Office*